United States Patent [19]

Gruber

[11] Patent Number: 4,470,417
[45] Date of Patent: Sep. 11, 1984

[54] HEAT THERAPY ORTHOSIS
[75] Inventor: Robert B. Gruber, Cincinnati, Ohio
[73] Assignee: Surgical Appliance Industries, Inc., Cincinnati, Ohio
[21] Appl. No.: 347,414
[22] Filed: Feb. 10, 1982
[51] Int. Cl.³ .............................................. A61F 7/00
[52] U.S. Cl. ............................ 128/402; 128/DIG. 15
[58] Field of Search ............... 128/399, 402, 379, 293, 128/DIG. 15, 78

[56] References Cited

U.S. PATENT DOCUMENTS

| | | |
|---|---|---|
| 850,281 | 4/1907 | Walter . |
| 2,584,302 | 2/1952 | Stein ............................... 128/399 X |
| 2,630,573 | 3/1953 | Rand . |
| 3,092,110 | 6/1963 | Duensing . |
| 3,307,535 | 3/1967 | Locke ................................... 128/78 |
| 3,501,616 | 3/1970 | Arron . |
| 3,518,995 | 7/1970 | Claff . |
| 3,849,802 | 11/1974 | Govaars . |
| 3,934,583 | 1/1976 | Hollingshead . |
| 4,099,524 | 7/1978 | Cueman ...................... 128/DIG. 15 |
| 4,121,582 | 10/1978 | Remiro . |

Primary Examiner—Stephen C. Pellegrino
Attorney, Agent, or Firm—Wood, Herron & Evans

[57] ABSTRACT

A low back orthosis having a heat reflective liner for providing simple and efficient heat therapy while maintaining restriction and providing support particularly to the iliac and lumbar spine.

2 Claims, 5 Drawing Figures

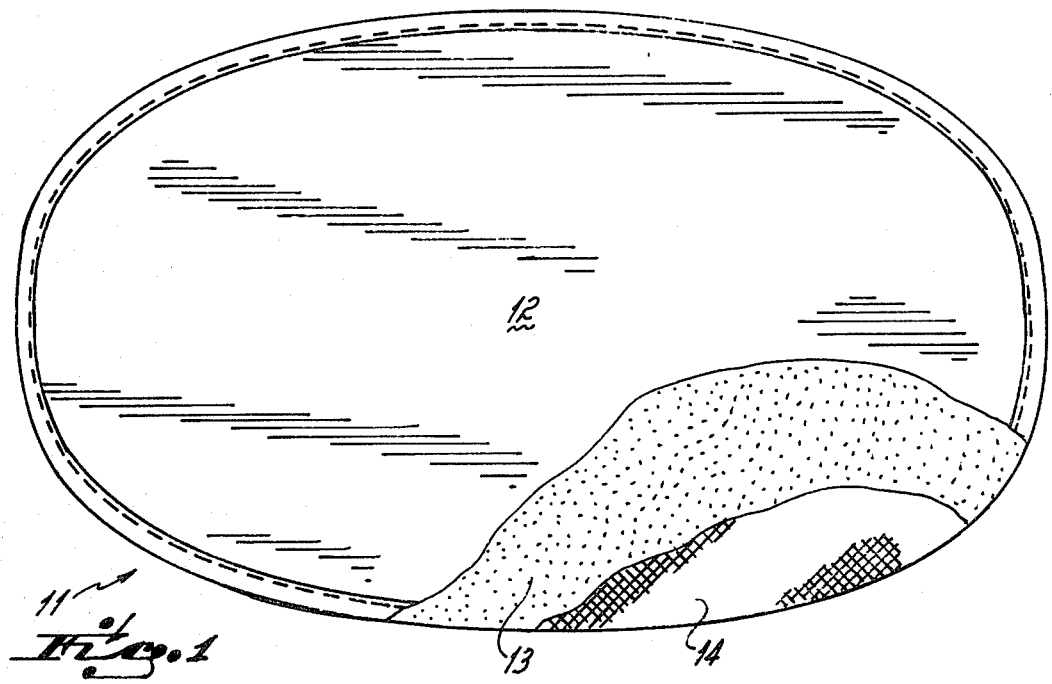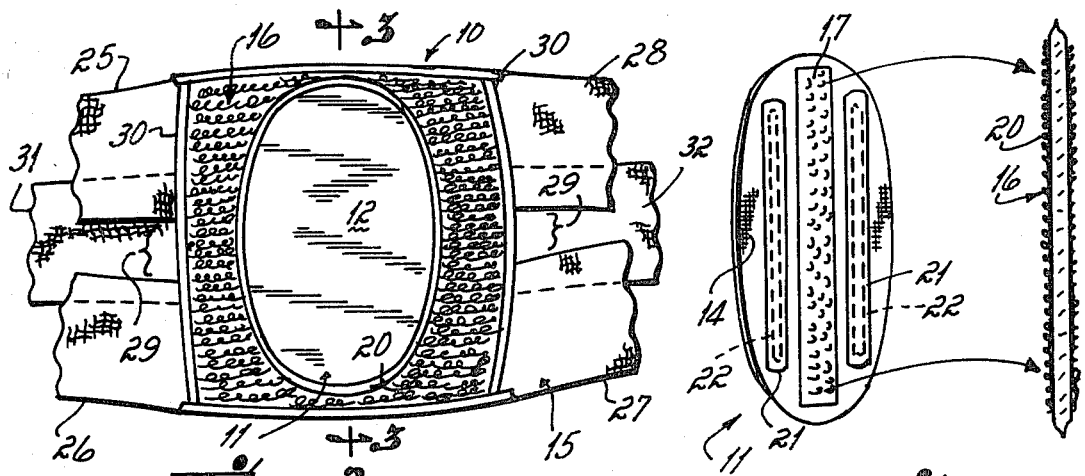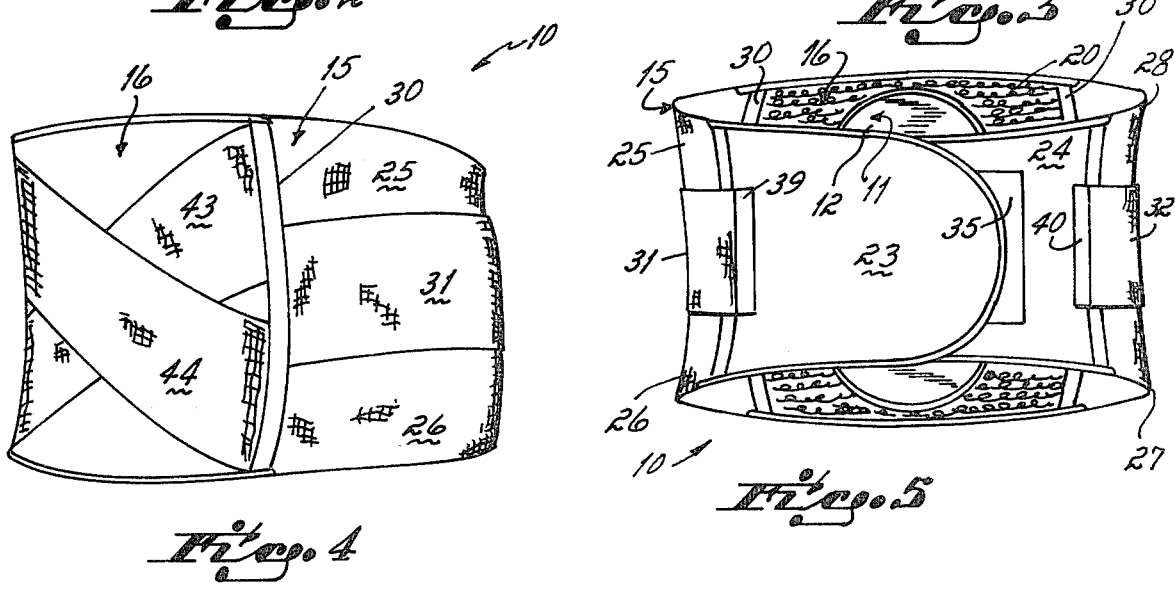

HEAT THERAPY ORTHOSIS

BACKGROUND OF THE INVENTION

This invention pertains to orthopedic appliances in general and relates to a low back orthosis having a removable heat-reflecting member for therapeutic heat treatment of the iliac and lumbo-sacral areas in particular.

In the treatment of many types of diseases and disorders of the body, it is often advantageous to keep the afflicted area warm, or more desirable still, at an elevated skin temperature. This is true of the treatment of arthritis, neuritis, muscular ailments, and certain mechanical bone disorders. This heat therapy typically takes the form of wrapping the area to be treated with a brace or bandage, or applying a pad to the region which by reason of a low thermal conductance limits the escape of body heat. Ointments and salves are often also applied to stimulate the skin surface and thereby generate a higher temperature in the treatment area.

The difficulty with therapy through ointments and salves is that the heat generation is relatively short-lived, requiring additional applications if a continuous warming is be to maintained. Salves and ointments are also messy and somewhat malodorous, further reducing their desirability as a therapeutic agent.

Bandages, braces and pads made of low thermal conductivity material do serve to reduce heat loss, but are generally relatively thick since the degree of thermal nonconductance is a function of thickness. This adds unnecessary cost, weight and bulk to the support brace.

SUMMARY OF THE INVENTION

It is thus a principle object of the present invention to provide a supportive and restrictive orthosis having a relatively flexible and lightweight heat-retaining member to effect simple and efficient heat therapy for an isolated body area while simultaneously providing the necessary restriction and support to the body. This objective is accomplished in accordance with certain principles of the invention, by providing a lightweight, thin, flexible heat-reflective liner interiorly of a compressive and supportive body-encircling orthosis. In a preferred form of the invention, the heat-reflecting liner, which is removable, is a thin sheet of plastic, such as mylar, having a thickness of 10 mils or less. For convenience, the heat-reflecting sheet is mounted on a thin foam pad fixed to a fabric backing. The aluminized layer is fixed to the foam pad only around the periphery, leaving an air gap between the foam pad and the interior surface of the aluminized layer.

In the disclosed embodiment of the invention, the orthosis includes a body encircling low back restricting and supporting band of fabric having a rear inelastic central fabric panel which engages the lumbo-sacral and iliac regions of the wearer's back. The fabric-backed foam pad to which the heat-reflecting liner is mounted is removably attached to the inwardly facing fabric surface of this central rear panel through the use of compatible Velcro fasteners. By providing a large Velcro section on the interior of the rear central panel of the orthosis, the wearer can adjustably position the thermal-reflective liner over the precise spot where heat therapy is desired.

The orthosis further comprises two opposed partially overlapping front panels connected to the central rear panel portion by intermediate side encompassing elastic panels. The front panels are covered on both sides with Velcro fastener compatible material. One front panel has a strip of Velcro fastener material at its terminis for adjustably fixing the lumbo-sacral orthosis in place on the wearer with the desired degree of restriction and support to the lumbo-sacral and iliac regions of the wearer.

Two opposed auxiliary elastic pulls are also fixed at one end to the rear central panel and overlap the respective side panels. The auxiliary elastic pulls each have Velcro fasteners attached at the other end, whereby the pulls can be stretched and adjustably fixed to the compatible material of the front panels for additional restriction and support to straighten the patient's low back region.

Criss-crossed elastic panels on the exterior of the rear central panel further enhance compressive support of this area.

The heat-reflecting liner, in combination with the aforementioned orthosis, thus provides an effective and efficient heat treatment orthosis which can be easily and simply applied by the patient, and which is not unnecessarily bulky or heavy.

BRIEF DESCRIPTION OF THE DRAWINGS

The objects and advantages of the invention will be further appreciated from the following detailed description of a preferred embodiment of this invention with reference to the accompanying drawings, in which:

FIG. 1 is a plan view, partially cut-away, of the heat-reflective liner;

FIG. 2 is an elevational view of the interior surface of the rear central panel of the heat treatment orthosis, showing the heat-reflecting liner mounted thereto.

FIG. 3 is a cross-sectional view along line 3—3 of FIG. 2, the heat reflecting liner being detached therefrom and viewed from the rear.

FIG. 4 is an elevational view of a side and rear panel of the heat-treating orthosis with the thermal liner shown in phantom.

FIG. 5 is a front elevational view of the heat-treating orthosis.

DETAILED DESCRIPTION OF THE PREFERRED EMBODIMENT

Referring now to FIGS. 1 and 2, the heat treatment orthosis of the invention is generally indicated at 10. In this preferred embodiment, the heat reflecting member 11 is in the form of a thin pad having an outwardly facing heat reflecting liner 12. The liner 12 may be formed of any suitable material which is capable of reflecting heat back to the covered body surface. To this end, a liner 12 composed of an aluminized mylar approximately 10 mils in thickness has proven effective to provide the localized area heat therapy in a supportive, compressive orthosis which is the primary objective of this invention. The aluminized mylar disclosed for the heat liner 12 is readily obtainable on the commercial market.

The pad may be composed of any suitable material. A pad having a thin layer of resilient foam material 13 with a fabric covering 14 has proven satisfactory for the practice of this invention. The liner 12 is advantageously fixed, as by stitching, around the periphery of the pad, leaving the liner 12 free from any attachment intermediate its edges. The heat reflecting member 11 is lightweight, flexible and thin and effectively reflects body heat to raise the temperature of the underlying skin. The heat reflecting member 11 has been formed in a roughly oval shape to facilitate its application in a low back orthosis. The heat reflecting member 11 is shown in combination with a band or support indicated generally at 15 which has been dimensioned to encircle the lower back region of a user.

The heat reflecting member 11 is adapted to be removably attached to the interior surface of the rear central panel 16 of the support 15. The support 15 may thus be used for simple compressive and restrictive support as well as for heat therapy treatment, as desired.

Simple removable attachment has been accomplished by providing the heat reflecting member 11 and the rear central panel 16 of the support 15 with a Velcro fastener. This fastener here takes the form of a single rectangular mat of nylon hooks 17 fixed along the major axis of the back of the member 11 which cooperates with the soft nap mat 20 covering the inwardly facing surface of the central panel 16. This patented fastener is pressure-responsive, and is operated by pressing the cooperating mats 17 and 20 together for fastening and pulling them apart for unfastening. A large mat 20 is provided on the central portion 16 to enable simple attachment of the heat reflecting member 11 for placement over the precise area where heat therapy is desired.

As shown in FIG. 3, pockets 21 may be provided in the rear of the heat reflecting member 11 into which rigid stays 22 (shown in phantom) can be inserted if additional orthopedic support is deemed necessary or is desirable.

Referring now to FIGS. 4 and 5, the support 15 is preferably formed of a fabric material having an inelastic rear central panel 16 which overlies the iliac and lumbar regions of the spine and inelastic front panels 23 and 24. The central panel 16 is of increased vertical dimension compared to the front panels 22 and 23. The front panels 23 and 24 are overlying when the support 15 is in place.

Both the front panels 23 and 24, and the central panel 16, are formed of the same soft relatively non-extensible fabric material having a nap which is cooperable with Velcro hook elements. Length-wise stretch of the support 15 is provided by elastic side panels 25, 26, 27 and 28. Two panels are located intermediate the front panels 23 and 24 and the rear central panel 16 on either side of the support 15. One end of each side panel is fixed along the upper or lower side edges 30 of the rear central panel 16, and the other end to the corresponding portion of the respective front panel 23 or 24, thereby following the general taper of the support 15. A small triangular shaped open area 29 thus remains between the elastic side panels of each side. Extra rigidity can be achieved for the rear central panel 16 by providing reinforcing stays (not shown) along the side edge 30.

The front panels 23 and 24 of the support are closed about the patient by overlapping the end surfaces. A mat of Velcro hook material 35 fixed at the end of one front member acts to fasten the support 15 when pressed against the compatible nap mat covering the exposed surface of each of the front members 23 and 24.

Additional support, in the way of straightening and restricting the torso, is also achieved through the use of two auxiliary elastic pulls 31 and 32. One pull is fixed at one end to either side of the rear central panel 16 to overlie the elastic panels 25, 26, and 27, 28, respectively. The auxiliary elastic pulls 31 and 32 are each provided with Velcro hook mats 39 and 40 at the opposite end for fastening with the compatible mat of the front panels 23 and 24. A patient is thus able to quickly and easily adjust the support 15 to produce the desired restriction and compression for this region. The orthosis will, in general, fit all sizes.

Further compressive support for the lumbar and iliac area is provided by elastic panels 43 and 44. As shown in FIG. 4, the panels 43 and 44 are fixed about the rear central panel 16 so as to criss-cross over its exterior side. The panels 43 and 44 are made slightly smaller in length than the corresponding diagonals of the inelastic central panel 16 which they overlie. The elastic panels are consequently stretched when the support 15 is placed on the patient, thereby exerting additional supportive compression in this region.

The support 15 thus provides quick and simple adjustment for the desired degree of low back support with adequate flexibility remaining in the garment to permit relatively natural movement of the patient.

In application as a heat therapy orthosis 10, the heat reflecting member 11 is appropriately attached to the interior of the rear central panel 16 of the support 15. The support 15 is then positioned on the patient, and the front panels 23 and 24 overlapped and fastened closed. The auxiliary elastic side pulls 31 and 32 are fastened to the front panels 23 and 24 for additional compression.

Constant heat therapy of the lower spine is thus simply and effectively achieved. Furthermore, the support fits snugly about the patient, and being light in weight and relatively body-conforming, can be worn under ordinary clothing.

It can be appreciated that the orthosis described herein provides heat therapy in a unique manner which applicant believes is novel in application. The orthosis further provides a great degree of versatility when combined with an orthopedic appliance in this manner. Although this orthosis has been described in terms of a low back support, it is contemplated that other orthotic devices can be simply adapted to provide heat therapy in the disclosed manner and are thus within the scope of this invention.

The foregoing is therefore considered as illustrative of the principles of this invention. Since numerous modifications and changes will be apparent to those skilled in the art, all suitable modifications and equivalents of the invention which fall within the scope of the following claims may be deemed to be encompassed by this invention.

What is claimed is:

1. A heat treatment low back orthosis comprising:
    a flexible fabric band dimensioned and configured to encircle the lower back region of a user for restricting and supporting the user's lumbar and iliac regions, said flexible fabric band comprising:
    a rear central panel,
    two inelastic front panels,
    at least one elastic side panel joining each of said front panels to said rear central panel,
    fastening means for said front panels for mutual interconnection,
    at least two auxilliary elastic panel pulls, having opposed ends,
    said pulls being respectively fixed at one end to opposite lateral sides of said rear central panel, said pulls having fastening means on the unfixed end for connection to said front panels, and at least one elastic panel overlying said rear central panel, said elastic panel causing flexion in said rear central panel when said support is not in use, and a lightweight, flexible, thin liner of heat-reflecting metalized plastic mounted interiorly of said band proximate the body area to be treated for reflecting body heat back to said body area to raise the skin temperature thereof.

2. The orthosis of claim 1 having two elastic panels fixed to said rear central panel, said panels arranged in a criss-cross pattern across the face of said portion.

* * * * *